United States Patent
Bezemer et al.

(10) Patent No.: US 10,408,818 B2
(45) Date of Patent: Sep. 10, 2019

(54) CHEMICAL ANALYSIS OF URINE AND FECES VAPOR

(71) Applicant: KONINKLIJKE PHILIPS N.V., Eindhoven (NL)

(72) Inventors: Rick Bezemer, Amsterdam (NL); Nicolaas Lambert, Waalre (NL); Maria Estrella Mena Benito, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 5 days.

(21) Appl. No.: 15/529,238

(22) PCT Filed: Nov. 24, 2015

(86) PCT No.: PCT/EP2015/077550
§ 371 (c)(1),
(2) Date: May 24, 2017

(87) PCT Pub. No.: WO2016/083405
PCT Pub. Date: Jun. 2, 2016

(65) Prior Publication Data
US 2017/0328884 A1 Nov. 16, 2017

(30) Foreign Application Priority Data
Nov. 27, 2014 (EP) .................................... 14195208

(51) Int. Cl.
*G01N 33/497* (2006.01)
*A61B 5/00* (2006.01)
(Continued)

(52) U.S. Cl.
CPC ........... *G01N 33/497* (2013.01); *A47K 13/24* (2013.01); *A61B 5/207* (2013.01); *A61B 5/4255* (2013.01);
(Continued)

(58) Field of Classification Search
CPC .............................. G01N 33/497; E03D 9/007
See application file for complete search history.

(56) References Cited

U.S. PATENT DOCUMENTS

| 3,977,836 | A | * | 8/1976 | Matsuda | G01N 31/005 |
| | | | | | 436/113 |
| 5,131,261 | A | * | 7/1992 | Tou | G01N 15/08 |
| | | | | | 73/38 |

(Continued)

FOREIGN PATENT DOCUMENTS

| CN | 1928555 A | 3/2007 |
| EP | 1443323 A1 | 8/2004 |

(Continued)

OTHER PUBLICATIONS

Aathithan et al: "Diagnosis of Bacteriuria by Detection of Volatile Organic Compounds in Urine Using an Automated Headspace Analyzer With Multiple Conducting Polymer Sensors";Journal of Clinincal Microbiology, Jul. 2001, PP. 2590-2593.

(Continued)

*Primary Examiner* — Lisa M Caputo
*Assistant Examiner* — Alex T Devito (57) ABSTRACT

A gas sensor system is for use in, or in the vicinity of, a toilet, for detecting a target gas. A gas sensor detects a concentration of at least the target gas and a further, reference, gas which is received from a controlled gas release device. These concentrations are processed to obtain a concentration of the target gas relative to the concentration of the further gas by combining a change in the detected concentration of the target gas, a change in the detected concentration of the further gas, the sensitivity of the gas sensor system to the target gas and the sensitivity of the gas sensor system to the further gas. This approach avoids the (Continued)

need for extensive calibration operations to tune the sensor response to the environment in which it is used.

16 Claims, 3 Drawing Sheets

(51) Int. Cl.
  *A61B 5/20* (2006.01)
  *A47K 13/24* (2006.01)
  *G01N 33/493* (2006.01)
  *E03D 9/00* (2006.01)

(52) U.S. Cl.
  CPC ............ *A61B 5/6887* (2013.01); *E03D 9/007* (2013.01); *G01N 33/493* (2013.01); *G01N 2033/4975* (2013.01)

(56) References Cited

U.S. PATENT DOCUMENTS

| | | | |
|---|---|---|---|
| 2001/0041366 A1 | 11/2001 | Lewis et al. | |
| 2002/0182739 A1 | 12/2002 | Sadik et al. | |
| 2009/0261987 A1 | 10/2009 | Sun | |
| 2010/0061889 A1 | 3/2010 | Park | |
| 2011/0269632 A1 | 11/2011 | Haick et al. | |
| 2014/0023557 A1 | 1/2014 | Tian et al. | |
| 2015/0330958 A1* | 11/2015 | Carney | A61F 13/42 73/23.34 |
| 2016/0239624 A1* | 8/2016 | Short | G06F 19/18 |

FOREIGN PATENT DOCUMENTS

| | | |
|---|---|---|
| JP | 2003270242 A | 9/2003 |
| JP | 2005292049 A | 10/2005 |
| JP | 2009250799 A | 10/2009 |
| KR | 1020070029001 A | 3/2007 |
| WO | 2005024389 A1 | 3/2005 |
| WO | 2014098690 A1 | 6/2014 |

OTHER PUBLICATIONS

Arshak et al: "A Review of Gas Sensors Employed in Electronic Nose Applications"; Sensor Review, vol. 24, No. 2, 2004, pp. 181-198.
Dentoni et al: "Electronic Noses for the Qualitative and Quantitative Determination of Environmental Odours"; Chemical Engineering, vol. 30, 2012, pp. 211-216.
"Maple Syrup Urine Disease";2010 Red Urine, 2 Page Article.
"The Truth About Urine"; WebMD Article, Downloaded at http://www.webmd.com/urinary-incontinence-oab/truth-about-ruine on May 17, 2017, 2005-2017 WebMD, LLC, 5 page article.
Wilson:"Future Applications of Electronic-Nose Technologies in Healthcare and Biomedicine" Chapter 15 of "Wide Spectra of Quality Control" Edited by Dr. Isin Akyar; pp. 267-290, Published Jul. 2011.
Wilson et al: "Advances in Electronic Nose Technologies Developed for Biomedical Applications"; Sensors 2011, vol. 11, pp. 1105-1176.
Wongchoosuk et al: "Detection and Classification of Human Body Odor Using an Electronic Notse"; Sensors 2009, vol. 9, pp. 7234-7249.
Mantini et al: "Biological Application of an Electronic Noise"; Critical Reviews in Biomedical Engineering, vol. 28:pp. 481-485, 2000.

* cited by examiner

CHEMICAL ANALYSIS OF URINE AND FECES VAPOR

CROSS-REFERENCE TO PRIOR APPLICATIONS

This application is the U.S. National Phase application under 35 U.S.C. § 371 of International Application No. PCT/EP2015/077550, filed on Nov. 24, 2015, which claims the benefit of European Patent Application No. 14195208.5, filed on Nov. 27, 2014. These applications are hereby incorporated by reference in their entirety herein.

FIELD OF THE INVENTION

The invention relates to the analysis of urine or feces, for use in enabling medical indications to be provided. It relates in particular to the analysis of urine and feces gases.

BACKGROUND OF THE INVENTION

Urine is one of the most useful health condition indices within the human body. Changes in the urine color, odor, and consistency can provide important clues about the person's health status. Urine reflects all of the inner workings of the body and contains a wide variety of compounds and metabolic by-products.

Urine is an important part of the body's disposal process. Its job is to remove the extra water and water-soluble waste the kidneys have filtered from the blood. The urine is there primarily to remove toxins that would otherwise build up in the body. Additionally, urine can reveal what the person has been eating and how much they have been drinking As such, the analysis of urine has, for hundreds of years, been one of the ways physicians have assessed various health conditions. As an example, increased concentration of ammonia in urine reflects dehydration. The concentration of ammonia is directly proportional to the extent of dehydration. While ammonia volume is related to fluid intake, it is the concentration of ammonia that reflects the (de)hydration status.

A regular urine test may be done to check the different components of urine. The test can give information about person's health and problems they may have. However urine tests suffer from different issues, including awkward handling of urine, and costly and time-consuming detection of the substance of interest. Therefore, urine tests are only performed sporadically and not automatically during every toilet visit. They are therefore not suitable for tracking day-to-day changes in a person's health status (e.g. for tracking dehydration in elderly).

Recent advances in gas sensing technology, signal processing, and diagnostic algorithms have created chemical sensing and identification devices called "electronic noses" or "e-noses". These sensor devices are capable of detecting, identifying, and discriminating many types and sources of a wide diversity of chemical species and mixtures of compounds, present in sampled air derived from any source. Therefore, electronic noses are ideal instruments for biomedical uses because of their versatility, low cost, rapid output of results, and capability of continuous operation for physiological monitoring purposes.

A problem with e-nose technology is that, without knowledge of the environment (temperature, volume, flow, distance to source) in which the e-nose is used, concentration of target gases cannot be determined. Furthermore, the output of an e-nose is also affected by small variations in common air constituents such as water or carbon dioxide and variations in temperature.

US 2010/0061889 discloses an apparatus and method for providing results of urine and/or gas analysis. It describes a system with a sensor either in contact with urine or detecting feces gas. The problem of calibration with respect to the nature of the environment in which the sensor is used is not addressed.

SUMMARY OF THE INVENTION

The invention is defined by the claims.

According to an aspect of the invention, there is provided a gas sensor system for use in, or in the vicinity of, a toilet, for detecting a target gas, comprising:

a gas sensor for detecting a concentration of at least the target gas and a further gas, wherein the further gas is received from a controlled gas release device for releasing the further gas at a controlled rate; and a controller for processing the detected concentration of the target gas and the further gas, wherein the controller is adapted to obtain a concentration of the target gas relative to the concentration of the further gas by combining:

a change in the detected concentration of the target gas;
a change in the detected concentration of the further gas;
the sensitivity of the gas sensor system to the target gas; and
the sensitivity of the gas sensor system to the further gas.

In this way, changes in two gases (one of which is a target) are monitored.

The problem of the environment affecting the measurements of an e-nose is addressed by this approach, and it enables the use of e-nose technology to quantify the concentration of target gases in larger rooms (like the cloakroom or bathroom) with undefined environmental characteristics. This eliminates the need for sampling of urine or feces and/or contact with the sample. The sensor system may for example be integrated into a suspended toilet freshener block often placed hanging on the inside of the toilet. The sensor system does not need to have any impact on the way the toilet is used.

The gas sensor may comprise a single unit for detecting both the target gas and the further gas, or else separate dedicated sensors may be used.

The system may enable an unobtrusive assessment of a person's health status (e.g. hydration status) during normal toilet use. Health information may be derived from the obtained signals in a personalized way, for example by reading out the information through a mobile telephone application.

The target gas may comprise ammonia, acetone, nitric oxide or volatile organic compounds.

These can provide different medical indications.

The further gas has a known baseline concentration and the controller is adapted to obtain a concentration of the target gas relative to the baseline concentration, thereby to determine a calibrated concentration of the target gas.

The further gas may for example comprise a gas component of an air freshener, wherein the air freshener is in, or in the vicinity of, the toilet. The air freshener in this way is used to create a reference baseline, so that the detection of the target gas can be calibrated to the environment in which the sensor is located. The further gas may be maintained at a substantially constant concentration by carrying out a controlled release. Even if the absolute concentration of the further gas is not known, it can still be used to correct the measured relative concentration of the target gas for changes in humidity, temperature, or the gradual desensitization of the sensors, for example.

The further gas may be used only for the purposes of the analysis system (i.e. not part of a freshener gas). The further gas may be a pure gas which is released at a constant rate to maintain a steady concentration (resulting from the free outflow of gas from the toilet).

The concentration Ca of the target gas relative to the baseline concentration Cr of the further (reference) gas may be obtained as:

$$Ca/Cr = (\int [a(t)-a0]dt / \int [r0-r(t)]dt) Sr/Sa$$

in which a0 is a sensed concentration of the target gas at the start of a sensing cycle, a(t) is the sensed concentration of the target gas over time, r0 is a sensed concentration of the further gas at the start of the sensing cycle, r(t) is the sensed concentration of the further gas over time, Sa is the sensitivity of the has sensor to the target gas and Sr is the sensitivity of the sensor to the further gas, and wherein the integration is over a sensing time period.

An increase in the target gas concentration (which manifests itself as an increase in a(t)) is accompanied by a drop in the concentration of the further gas (which manifests itself as a drop in r(t) from the previous baseline sensed level r0 corresponding to the known baseline).

The target gas may comprise many constituent parts. If the sensing is based only on one constituent part, or a sub-set of the constituent parts, then the equation above can be adjusted (or the value of Sa can be adjusted) to take account of the fact that the sensed target gas represents a larger overall target gas presence which is displacing the further (reference) gas. Instead, multiple different constituent parts may be sensed, which in total displace the further (reference) gas. Thus, the equation above may be extended to include multiple target gases, which together displace the further (reference) gas.

In this way, a simple integration of sensor signals during a sensing period, followed by basic algebraic functions, can obtain the calibrated sensor measurement for the target gas.

In another aspect, there is the additional option of measuring the relative concentration between two target gases, of unknown concentration.

The concentration Ca of the a first target gas relative to the concentration Cb of a second target gas is then obtained as:

$$Ca/Cb = (\int [a(t)-a0]dt / \int [b(t)-b0]dt) Sb/Sa$$

in which a0 is a sensed concentration of the first target gas at the start of a sensing cycle, a(t) is the sensed concentration of the first target gas over time, b0 is a sensed concentration of the second target gas at the start of the sensing cycle, b(t) is the sensed concentration of the second target gas over time, Sa is the sensitivity of the gas sensor to the first target gas and Sb is the sensitivity of the sensor to the second target gas, and wherein the integration is over a sensing time period.

In this case, there is an increase in the target gas concentration (which manifests itself as an increase in a(t)) as well as an increase in the second target gas concentration (which manifests itself as an increase in b(t)).

Again, a simple integration of sensor signals during a sensing period, followed by basic algebraic functions, can obtain a concentration ratio. This concentration ratio may be used for diagnostic purposes, rather than using an absolute concentration of a reference gas.

The second target gas may also comprise ammonia, acetone, nitric oxide or volatile organic compounds.

The sensor preferably comprises an electronic nose.

Examples of the invention also provide a gas sensing method for detecting a target gas system in or in the vicinity of a toilet, comprising:

receiving the target gas, and receiving a further gas from a controlled gas release device which releases the further gas at a controlled rate;

detecting a concentration of at least the target gas and the further gas;

processing the detected concentration of the target gas and the further gas, thereby to obtain a concentration of the target gas relative to the concentration of the further gas by combining:

a change in the detected concentration of the target gas;
a change in the detected concentration of the further gas;
the sensitivity of the gas sensor system to the target gas; and
the sensitivity of the gas sensor system to the further gas.

Since the further gas has a known baseline concentration the method may comprise obtaining a concentration of the target gas relative to the baseline concentration thereby to determine a calibrated concentration of the target gas.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a gas sensor system for use in, or in the vicinity of, a toilet, for detecting a target gas. A gas sensor detects a concentration of at least the target gas and a further gas which is received from a controlled gas release source. This further gas functions as a reference gas. These concentrations are processed to obtain a concentration of the target gas relative to the concentration of the further gas by combining a change in the detected concentration of the target gas, a change in the detected concentration of the further gas, the sensitivity of the gas sensor system to the target gas and the sensitivity of the gas sensor system to the further gas. This approach avoids the need for extensive calibration operations to tune the sensor response to the environment in which it is used.

The invention may be implemented as electronic nose-based system and method, for assessment of changes in urine or feces gas concentration, for example to track changes in a person's hydration status. The invention can also be applied for other biomedical purposes in which the concentration of a specific biomarker is important rather than only its presence.

The system enables the use of e-nose technology to quantify the concentration of target gases in larger rooms (like the toilet) with undefined environment. This eliminates the need for sampling of urine or feces and/or contact with the sample and therefore allows integration into a regular toilet block-like embodiment, for example hanging on the inside of the toilet while using the toilet in a normal fashion. The system is capable of automatic and quantitative analysis of different urine/feces components, and may then provide real-time information of the physiological/health condition of the toilet's user.

Figure 1:
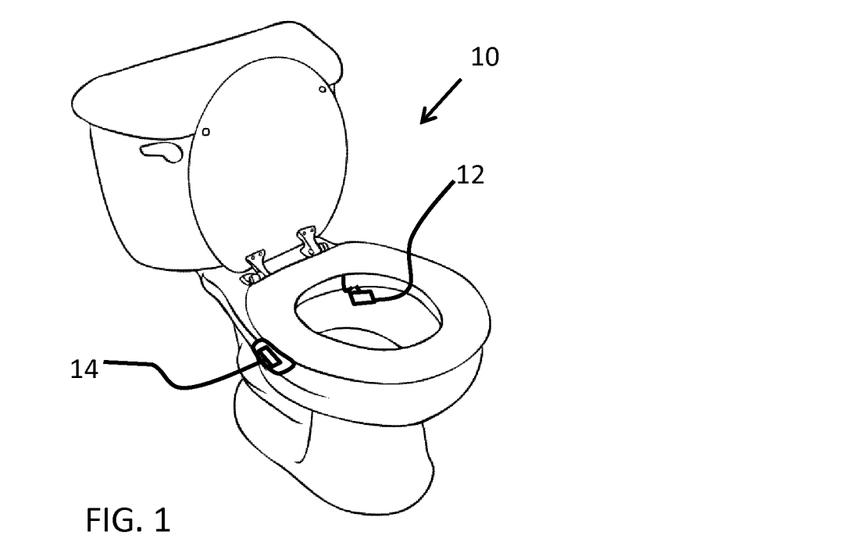
FIG. 1 shows a toilet which houses a sensor system in accordance with an example of the invention.

FIG. 1 shows a toilet 10.

A first set of examples make use of a gas release device 12 which is suspended in the toilet bowl. The gas release device is adapted to provide a controlled release of a reference gas. In one example, the gas release device is a toilet freshener, and the reference gas is a part of the toilet freshener gases. Alternatively, the gas release device may release a gas which has no odor and is instead chosen only because it can be sensed easily. In this case, the gas release device does not need to perform a toilet freshening function.

The gas release device releases the reference gas into the volume of the toilet bowl.

The housing for the gas release device (e.g. toilet freshener) also includes a gas sensor, for example in the form of an electronic nose. The gas sensor is thus for use in the toilet bowl or at least in the vicinity of the toilet. It is for detecting at least two gases.

A second concept does not make use of a reference gas, but instead is based on detection of two target gases.

This second concept may be used with only a sensor system, and with no need for a gas release device such as a toilet freshener. However, this second concept may be combined with the gas release device method described above to provide additional measurement options.

In the examples above, there is sensing of at least two gases. A first gas is a target gas, the concentration of which is of interest for providing a health diagnosis. A second (further) gas is a reference gas, as mentioned above. In an example which makes use of a toilet freshener, the second gas can be an air freshener gas produced by the toilet freshener. This functions as a reference gas.

In the second concept, a first gas is a target gas. A second (further) gas is another target gas, and the detection of the two gases may be used to obtain a measure of relative concentration. The additional use of a reference gas as in the examples above enables conversion to absolute concentration values The gas sensor can be a single device capable of detecting multiple gases or it can be multiple separate electronic gas sensors, each for a specific gas detection.

The sensor gives a "detected concentration" result. This would need to be calibrated in order to derive real concentration values. Thus, the term "detected" concentration is used to refer to a sensor reading. In the approach of this invention, the detected concentration of the target gas and the detected concentration of the second, reference, gas are processed to obtain a real i.e. calibrated concentration of the target gas relative to the real concentration of the further, reference, gas by monitoring changes in the detected concentration of the target gas and changes in the detected concentration of the further gas. The sensitivities of the gas sensor system to the two gases are also used.

The target gas (or each target gas if there are multiple target gases) may for example comprise ammonia, acetone, nitric oxide or volatile organic compounds.

FIG. 1 also shows the toilet seat provided with a weighing scale system 14. As discussed further below, this is one possible way for automatic detection of which user (within the household) is using the toilet. Other ways are of course possible, including manual input by the use of their identity. The use of weight measurement can also give additional information of interest for interpreting the sensor signals. For example, weight loss can be monitored to estimate urine output. Furthermore, using a smart analysis of the weight decay curve, it may also be possible to distinguish between defecation (sudden drop in weight) and urination (gradual decline in weight).

The signal output of the gas sensor is for example analysed by pattern recognition algorithms.

The reference gas occupies the toilet space with a known real concentration. When the toilet is used, a part of the reference gas is replaced by urine/feces gas. By measuring both the lowering of the reference gas concentration and the rise in the gas concentration of the urine/feces vapor, the concentration of the molecule of interest can be determined.

This ratio based method enables the use of e-nose technology to quantify the concentration of a molecule of interest in a toilet, regardless of for example the toilet room size and thus vapor dilution or temperature.

The gas sensor comprises an encased array of sensor elements. In the examples which makes use of a gas release device, the gas sensor may be integrated into the housing of the gas release device (e.g. toilet freshener block), so as to come in contact with urine/feces gas flow in the toilet. Sensors suitable for detection of urine/feces gases can be based on conducting and non-conducting materials, arranged in a matrix of conducting and non-conducting regions, e.g. metal oxide field effect transistor (MOSFET), piezoelectric devices, etc.

Each sensor element in the array has different characteristics. The compounds of interest are adsorbed on the sensor surface and transient response is produced as the compounds from the gas interact with the active material at the surface of the sensor. A specific response is recorded by the electronic interface.

The pattern of response across all the sensor elements in the array is used to characterize and identify a particular target gas.

Examples of the analysis are given below based on the sensing of two gases. However, the approach can be extended to more gases, and this may lead to more accurate results and/or more possible diagnostic information to be derived.

Figure 2:
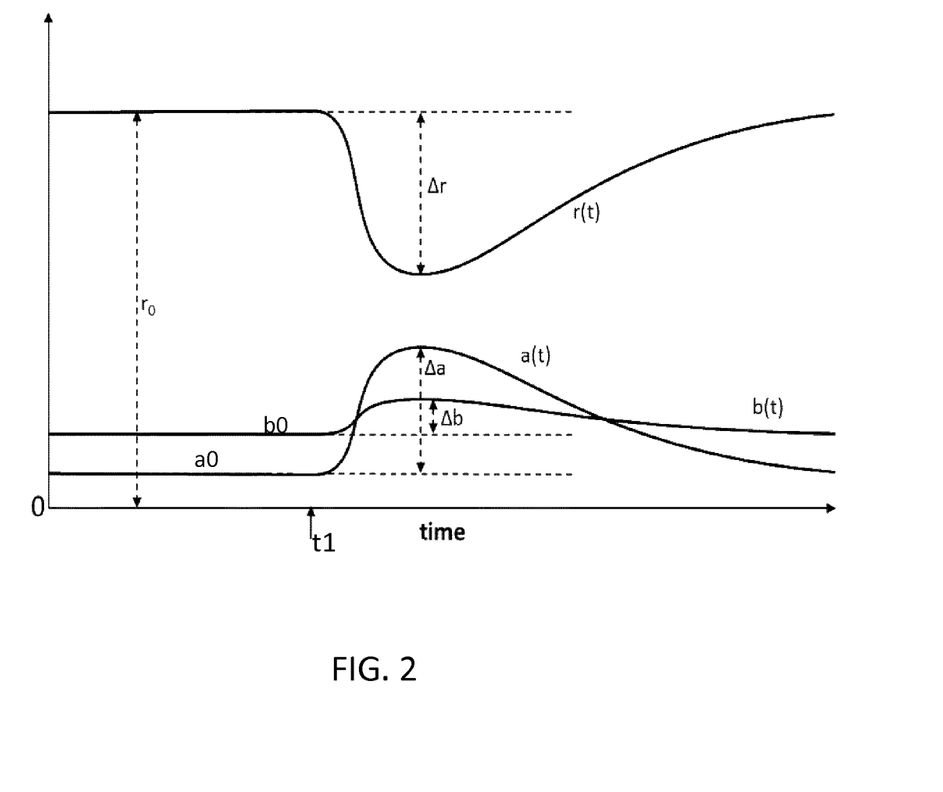
FIG. 2 shows sensor signals and is used to explain different processing approaches in accordance with examples of the invention.

FIG. 2 shows an illustration of an example measurement. The variations in concentration are shown exaggerated for clarity.

The three plots r(t), a(t) and b(t) are gas sensor signals for gases r, a and b. These show detected concentration levels. However, the way these detected levels correlate to the true concentration will depend on the nature of the sensing volume. Component r(t) is a reference component that comes from the sensor unit itself, namely the air freshener gas as explained above.

It has a constant concentration, giving rise to the signal $r_0$ leading up to the beginning of toilet use at time t1.

Components a(t) and b(t) are target gases which are associated with urine or feces. They each have a different baseline value a0 and b0 which represents their concentration in air (or in the reference gas if used). Components a(t), b(t) and r(t) all change during toilet use.

The background levels of the reference gas r lower, while the levels of a and b rise. As shown in FIG. 2, the two target gases a and b have different concentrations and/or they are associated with different gas sensor sensitivities. The detected reference gas concentration drops by at most Δr, while the detected target gas concentrations increase by at most Δr and Δb.

When the system is based on the analysis of one target gas a and the reference gas r, the concentration of, for example, component a, Ca, can be determined via:

$$Ca = Cr(\int[a(t)-a0]dt/\int[r0-r(t)]dt)Sr/Sa$$

Cr is the known baseline concentration of the reference gas r and Sr and Sa are the sensitivities of the sensor array to the components r and a, respectively.

The integration can be performed over the whole period associated the toilet use or during a specific phase of the toilet use.

Alternatively, the second concept outlined above may be used. Instead of calculating the ratio between the appearance of the target gas and the reduction of the reference gas, the ratio between two markers in the urine and/or feces can be calculated to detect disturbances in urine concentration.

In this case, the signal processing is based on signals a and b.

In this case, the relative concentration of the two target gases can be given by:

$$Ca/Cb = (\int[a(t)-a0]dt/\int[b(t)-b0]dt)Sb/Sa$$

Again, the integration can be done over the whole period associated the toilet use or during a specific phase of the toilet use.

This is of interest if the ratio between two target gases provides information of diagnostic interest. However, the absolute concentrations may then also be obtained in the manner explained above by making use of a reference gas.

These integration functions provide the area between the curves and their respective baselines, representing a total concentration change over time (with units of concentration×time). An alternative is to process the maximum concentration change values $\Delta r$, $\Delta a$ and $\Delta b$ (with units of concentration).

Figure 3:
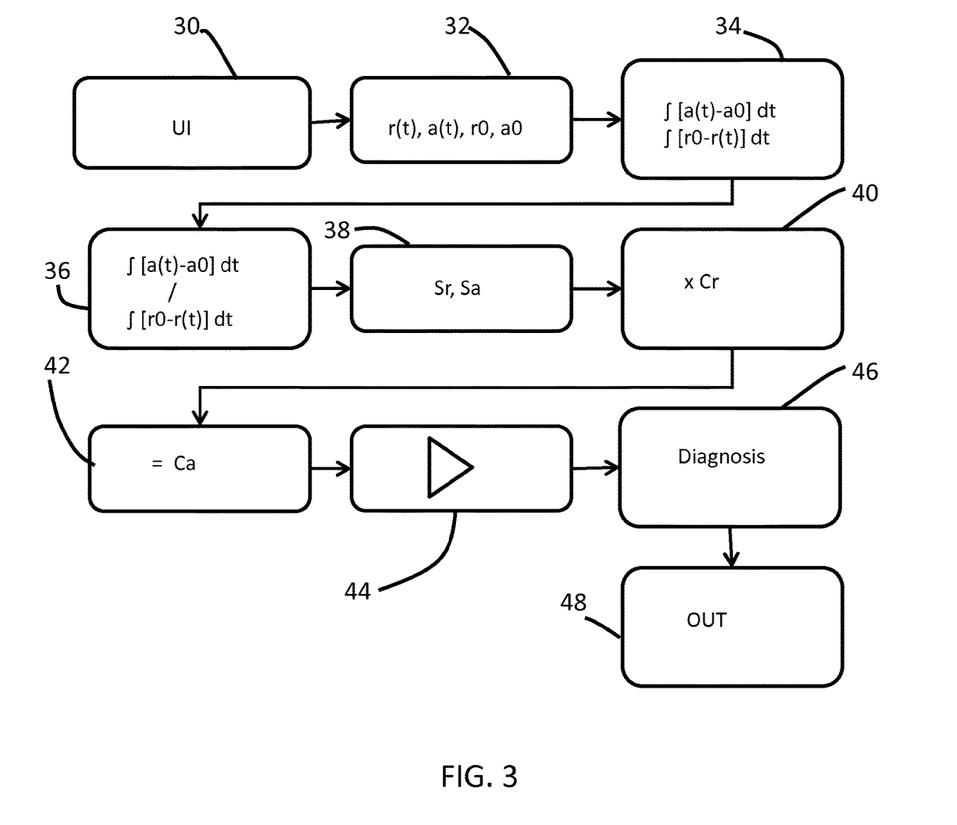
FIG. 3 shows a sensor signal processing method in accordance with an example of the invention.

FIG. 3 shows the processing method, based on the use of a reference gas sensor.

In (optional) step 30, the user of the toilet is identified by a user interface ("UI"). As mentioned above, this may be based on a detected weight of the user, although this will only be appropriate for a small number of possible users with different weights. For home use, this will be likely, whereas for use in a care home, for example, this may not be appropriate. If there is only one user of the toilet (e.g. an en-suite toilet) then no user identification is needed.

A user may instead identify themselves by pressing a button allocated to them on the toilet, or there may be automatic recognition based on wireless recognition of an identity device (such as an RFID tag) carried by the user. The user may identify themselves by operating an application on their mobile phone which advises the system of the user identity. The system can then track trends associated with individual users.

In step 32, the baseline values a0 and r0 are measured and the sensor detections signals r(t) and a(t) are measured.

In step 34, the integrations are carried out.

In step 36, the ratio between the integration results is obtained.

In step 38, correction based on the sensitivity values Sr and Sa is made.

In step 40, the multiplication by the known reference baseline concentration is carried out, to provide the concentration Ca in step 42.

In step 44 a comparison is made with a reference value or values, so that in step 46 a diagnosis can be made. These reference values are for example obtained from a 'normal' population or they can be obtained during previous toilet visits.

In step 48, an output system provides information of a diagnostic relevance to the patient or to a caregiver. This can then be used to make a diagnosis or monitor disease progression. This may comprise an upload to a mobile phone application, or a display output, or generation of a text or email message. Any suitable user interface can be used to deliver information to the patient or a caregiver.

Figure 4:
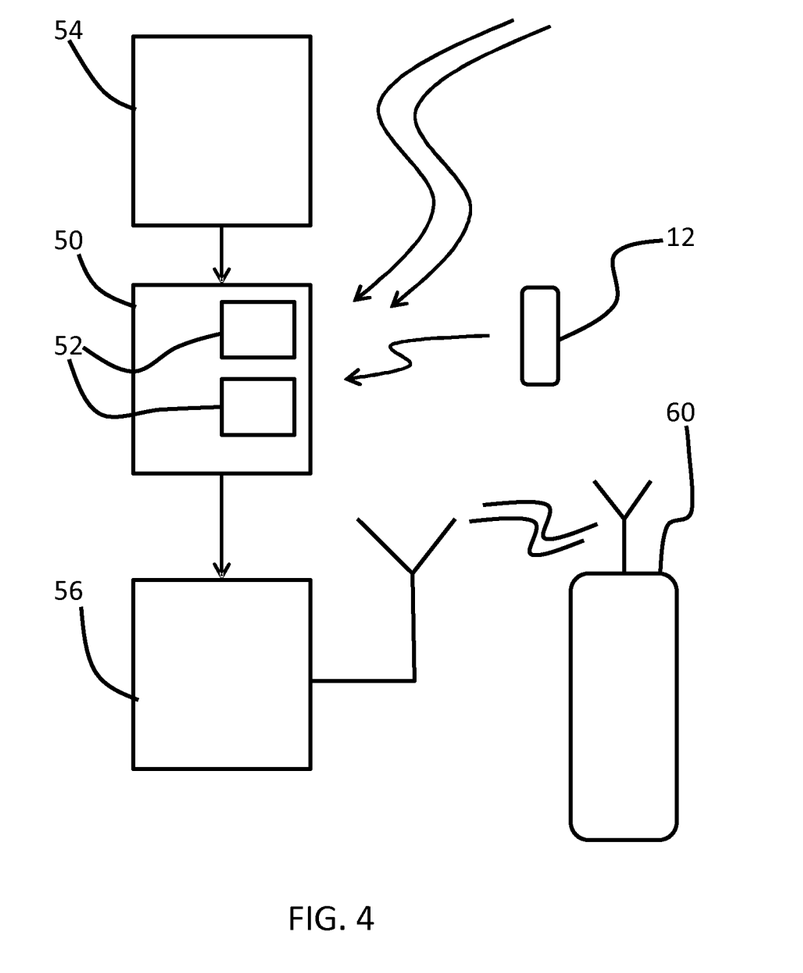
FIG. 4 shows a sensor system in accordance with an example of the invention.

FIG. 4 shows one example of the the system.

The gas sensor system 50 has at least two sensor elements 52, which may be separate sensors or different sensing regions of a single sensor. The system optionally receives an input form a user interface 54 which identifies the user, as discussed above.

The gas sensor signals are provided to a controller 56, such as a microprocessor 56, which implements the algorithms explained above. It may additionally implement a diagnostic analysis, although the diagnostic analysis can instead be performed later based on the information of diagnostic relevance which is generated by the system.

The information to be output, which may be the concentration information Ca and Cb, or the full sensing data (i.e. r(t), a(t) and b(t)), or the diagnosis information for example relating to a level of hydration, is transmitted to the user. In the example shown, this is by a wireless link 58 to a mobile telephone 60 of the user.

The invention proposes an unobtrusive system and method which enables real-time urine or feces gas analysis to be carried out. It may also perform real time analysis and diagnostic analysis to monitor the health condition of the toilet user, such as the hydration level.

The problem of e-nose technology, that knowledge of the environment in which the e-nose is used (temperature, air composition, volume, flow, distance to source) conventionally needs to be known, is addressed. The use of e-nose technology is thus able to be used to quantify the concentration of target substances in larger rooms (like the toilet) with undefined and variable environment.

The invention can be used for monitoring a range of conditions. One important application is dehydration monitoring for the elderly at home. The concentration of ammonia in urine (which one can smell very well), is directly proportional to the extent of dehydration. Furthermore, if urine is particularly pungent, for example with an ammonia scent, it can be due to an infection or urinary stones. Menopause, some sexually transmitted diseases, and certain metabolic disorders may also increase the ammonia scent. Diabetics might notice that their urine smells sweet, because of excess sugar. Also some genetic conditions causes urine to smell sickeningly sweet. Foul smelling urine may be due to bacterial infection and musty smelling urine can be related to liver diseases and certain metabolic disorders.

Multiple groups have used electronic nose technology for recognition of disease in vivo. Identification of unique molecular markers, volatile metabolites, associated with particular diseases is an extremely effective and powerful tool for the early detection of diseased tissues and infectious agents in the human body. Examples of descriptive aromas have been documented in numerous reports that associate connections between (un)usual specific human odors or aromas and particular human diseases and disorders, e.g. musty fish aroma breath can be related to liver failure, ammonia smell in urine can be linked to bladder infections, etc.

As discussed above, embodiments make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

As explained above, a second concept is to measure the relative concentration between two target gases. In this case, there is provided a gas sensor system for use in or in the vicinity of a toilet, for detecting a concentration ratio between two target gases, comprising:

a gas sensor for detecting a concentration of the first and second target gases, and a controller for processing the detected concentration of the first and second target gases, wherein the controller is adapted to obtain a concentration of the first target gas relative to the concentration of the second target gas by combining:

a change in the detected concentration of the first target gas;

a change in the detected concentration of the second target gas;

the sensitivity of the gas sensor system to the first target gas; and the sensitivity of the gas sensor system to the second target gas.

The concentration Ca of the first target gas relative to the concentration Cb of the second target gas is obtained as:

$$Ca/Cb = (\int [a0-a(t)]dt / \int [b(t)-b0]dt) Sb/Sa$$

in which a0 is a sensed concentration of the first target gas at the start of a sensing cycle, a(t) is the sensed concentration of the first target gas over time, b0 is a sensed concentration of the second target gas at the start of the sensing cycle, b(t) is the sensed concentration of the second target gas over time, Sa is the sensitivity of the has sensor to the first target gas and Sb is the sensitivity of the sensor to the second target gas, and wherein the integration is over a sensing time period.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A gas sensor system for use in, or in the vicinity of, a toilet, for detecting a target gas arising from use of the toilet, comprising:
    a controlled gas release device for releasing a further gas at a controlled rate;
    a gas sensor for detecting a concentration of at least the target gas arising from use of the toilet and the further gas; and
    a controller for processing the detected concentration of the target gas and the further gas, wherein the controller is adapted to obtain a concentration of the target gas relative to a baseline concentration of the further gas through: $(\int [a(t)-a0]dt / \int [r0-r(t)]dt) Sr/Sa$ where $\int$ represents integration over a sensing time period, a0 is a sensed concentration of the target gas at a start of a sensing cycle, a(t) is a sensed concentration of the target gas over time, r0 is a sensed concentration of the further gas at the start of the sensing cycle, r(t) is a sensed concentration of the further gas over time, Sa is a sensitivity of the gas sensor to the target gas, and Sr is a sensitivity of the gas sensor to the further gas.

2. The system as claimed in claim 1, wherein the sensor is adapted to detect a target gas which comprises ammonia, acetone, nitric oxide or other volatile organic compounds.

3. The system as claimed in claim 1, wherein the controller is adapted to assume a known baseline concentration for the further gas, and is adapted to obtain a concentration of the target gas relative to the baseline concentration thereby to determine a calibrated concentration of the target gas.

4. The system as claimed in claim 1, wherein the controlled gas release device comprises an air freshener device which is in the vicinity of the toilet.

5. The system as claimed in claim 1, wherein the gas sensor is adapted to detect a concentration of two or more target gases.

6. The system as claimed in claim 5, wherein the gas sensor is adapted to detect a concentration of a second target gas which comprises ammonia, acetone, nitric oxide or other volatile organic compounds, different to the target gas.

7. The system as claimed in claim 1, wherein the sensor comprises an electronic nose.

8. The system as claimed in claim 1, wherein the controller is adapted to determine the concentration of the target gas relative to the baseline concentration of the further gas based on a ratio of the change in the detected concentration of the target gas to the change in the detected concentration of the further gas.

9. The system as claimed in claim 1, wherein the controller is adapted to determine the concentration of the target gas relative to the baseline concentration of the further gas based on a ratio of the change in the sensitivity of the gas sensor system to the further gas to the sensitivity of the gas sensor system to the target gas.

10. The system as claimed in claim 1, wherein the controller is adapted to determine the concentration of the target gas relative to the baseline concentration of the further gas as a product of a first value and a second value, wherein first value is a ratio of the change in the detected concentration of the target gas to the change in the detected concentration of the further gas, and the second value is a ratio of the change in the sensitivity of the gas sensor system to the further gas to the sensitivity of the gas sensor system to the target gas.

11. A gas sensing method for detecting a target gas system in or in the vicinity of a toilet and arising from use of the toilet, comprising:

receiving the target gas and receiving a further gas from a controlled gas release device which releases the further gas at a controlled rate;

detecting a concentration of at least the target gas and the further gas; and processing the detected concentration of the target gas and the further gas, thereby to obtain a concentration of the target gas relative to a baseline concentration of the further gas through: $(\int[a(t)-a0]dt/\int[r0-r(t)]dt)Sr/Sa$ where $\int$ represents integration over a sensing time period, $a0$ is a sensed concentration of the target gas at a start of a sensing cycle, $a(t)$ is a sensed concentration of the target gas over time, $r0$ is a sensed concentration of the further gas at the start of the sensing cycle, $r(t)$ is a sensed concentration of the further gas over time, $Sa$ is a sensitivity of the gas sensor to the target gas, and $Sr$ is a sensitivity of the gas sensor to the further gas.

12. The method as claimed in claim 11, wherein the target gas comprises ammonia, acetone, nitric oxide or other volatile organic compounds.

13. The method as claimed in claim 11, wherein the target gas is selected from a group consisting of: ammonia, acetone or nitric oxide.

14. The method as claimed in claim 11, further comprising:

determining a first ratio of the change in the detected concentration of the target gas to the change in the detected concentration of the further gas;

determining a second ratio of the change in the sensitivity of the gas sensor system to the further gas to the sensitivity of the gas sensor system to the target gas; and determining the concentration of the target gas relative to the baseline concentration of the further gas by computing a product of the first ratio and the second ratio.

15. The method as claimed in claim 11, fur further comprising:

determining the concentration of the target gas relative to the baseline concentration of the further gas based on a ratio of the change in the detected concentration of the target gas to the change in the detected concentration of the further gas.

16. The method as claimed in claim 11, further comprising:

determining the concentration of the target gas relative to the baseline concentration of the further gas based on a ratio of the change in the sensitivity of the gas sensor system to the further gas to the sensitivity of the gas sensor system to the target gas.

* * * * *